United States Patent [19]

Stouffer

[11] Patent Number: 5,316,003

[45] Date of Patent: May 31, 1994

[54] METHOD AND APPARATUS FOR POSITIONING AN ULTRASONIC TRANSDUCER FOR LONGITUDINAL SCANNING OF AN ANIMAL OR CARCASS

[75] Inventor: James R. Stouffer, Ithaca, N.Y.

[73] Assignee: Animal Ultrasound Services, Inc., Ithaca, N.Y.

[21] Appl. No.: 918,979

[22] Filed: Jul. 24, 1992

[51] Int. Cl.⁵ ............................................... A61B 8/00
[52] U.S. Cl. ............................ 128/662.03; 128/660.07
[58] Field of Search ................... 128/660.01, 660.07, 128/661.03, 662.03

[56] References Cited

U.S. PATENT DOCUMENTS

| | | | |
|---|---|---|---|
| 3,496,764 | 2/1970 | Stouffer | 128/660.09 |
| 3,603,303 | 9/1971 | Stouffer | 128/660.01 |
| 3,688,564 | 9/1972 | McDicken | 73/620 |
| 3,709,029 | 1/1973 | Hurwitz | 73/624 |
| 3,722,263 | 3/1973 | Hautaniemi et al. | 73/622 |
| 3,742,756 | 7/1973 | Seager | 73/640 |
| 3,854,471 | 12/1974 | Wild | 128/660.09 |
| 3,964,296 | 6/1976 | Matzuk | 73/607 |
| 3,964,297 | 6/1976 | Jorgensen et al. | 73/609 |
| 4,094,306 | 6/1978 | Kossoff | 73/607 |
| 4,099,420 | 7/1978 | Stouffer et al. | 73/629 |
| 4,130,112 | 12/1978 | Frazer | 128/661.02 |
| 4,186,747 | 2/1980 | Iinuma | 128/660.08 |
| 4,359,055 | 11/1982 | Carlson | 73/631 |
| 4,359,056 | 11/1982 | Carlson | 73/631 |
| 4,545,385 | 10/1985 | Pirschel | 128/660.09 |
| 4,603,701 | 8/1986 | Chen | 128/662.03 |
| 4,625,731 | 12/1986 | Quedens et al. | 128/660.07 |
| 4,664,124 | 5/1987 | Ingle et al. | 128/660.02 |
| 4,772,346 | 2/1988 | Chen | 156/89 |
| 4,785,817 | 11/1988 | Stouffer | 128/660.07 |
| 4,870,970 | 10/1989 | Gray et al. | 128/660.09 |
| 4,931,933 | 6/1990 | Chen et al. | 364/409 |
| 5,014,713 | 5/1991 | Roper et al. | 128/664 |
| 5,028,440 | 7/1991 | Nissen | 426/2 |
| 5,078,147 | 1/1992 | Reid | 128/661.01 |
| 5,079,951 | 1/1992 | Raymond et al. | 73/602 |
| 5,140,988 | 8/1992 | Stouffer et al. | 128/660.01 |

FOREIGN PATENT DOCUMENTS 0337661 10/1989 European Pat. Off. .

OTHER PUBLICATIONS

"An Evaluation of Indices of Carcass Yield, Physical Composition and Chemical Composition in Swine; and Ultrasonic Measurement of the Longissimus Dorsi Area and Fat Thickness in Beef and Swine", Wayne Gillis, Jan. 1971.

"Pregnancy Detection and Changes During Gestation in Swine Determined with Ultrasound", T. Wongkhalaung, Jun. 1975.

"Grading Hog Carcasses: The CSB Ultra-Meater", CSB System.

"Commercial Adaption of Ultrasonography to Predict Pork Carcass Compositions from Live Animal and Carcass Measurements", Gresham et al, J. Anim. Sci, 1992, pp. 631-639.

(List continued on next page.)

*Primary Examiner*—Francis Jaworski
*Attorney, Agent, or Firm*—Barnard, Brown & Michaels

[57] ABSTRACT

The transducer positioning apparatus is for positioning an ultrasonic transducer on an animal or carcass to be evaluated by ultrasonic detection equipment. The apparatus includes a support arm. A tail bone pin extends from the first end of the support arm and is for locating the transducer with respect to a tail region of the animal or carcass. A back position pin extends from the support arm and is for locating the transducer with respect to a backbone of the animal or carcass. A transducer support unit is included at the second end of the elongated support arm and is for positioning the transducer such that the transducer is parallel to the backbone. The method of positioning an ultrasonic transducer or an animal or carcass to be evaluated by ultrasonic detection equipment, is novel. The method comprises positioning the transducer over a last few ribs of the animal or carcass such that the transducer is parallel to a backbone of the animal or carcass and the transducer is not parallel to fat interfaces of the animal or carcass.

10 Claims, 4 Drawing Sheets

OTHER PUBLICATIONS

"Using Ultrasound Objectively Evaluate Composition and Quality of Livestock", James Stouffer, 21st Century Concepts, pp. 49-53.

"Scamogram", Model 722, Ithaco, Inc., Ultrasonic Animal Scanner.

"Ultrasound for Disease Detection in Animals", J. Stouffer Seminar for FSIS-USDA, Sep. 18, 1985.

Ultrasonics for Live Lamb and Carcass Evaluation, J. R. Stouffer 1988 Proceeding Sheep Industry Development Program, Denver, Colo.

Syllabus—Animal Ultrasound Seminar & Wet-Lab—Oct. 13-15, 1989.

Ultrasonographic Evaluation of the Urninary System and Prostrate Gland in the Dog and Cat—R. Badertscher—Veterinary Imaging Professional.

Meat and Poultry Inspection—National Academic Press—1985.

Tendon and Ligament Ultrasound in the Equine Athlete—A. Kent Allen—Allen-Schneigder Equine Hospital.

A Review of Potential New Methods of On-Line Pork Carcass Evaluation—Forrest et al—J. Anim. Sci 1989—67:2164-2170.

A Review of Ultrasonic Applications in Animal Science—J. R. Stouffer—Journal of Clinical Ultrasound—vol. 5, Apr. 1977.

Ultrasound for Animal Evaluation—J. R. Stouffer—New York's Food and Life Sciences—vol. 10, No. 3, 1977.

Objective Technical Methods for Determining Carcass Value in Live Animals with Special Emphasis on Ultrasonics—J. R. Stouffer—World Review of Animal Production—1966.

Mild Exercise—Effect on Body Composition and Metabolism Stouffer et al—N.Y. State Journal of Med.—Aug. 1974.

Relationship of Ultrasonic Measurements and W-X-Rays to Body Composition—J. R. Stouffer—Animals of the N.Y. Academy of Sci, vol. 110, Part I. Pp. 31-39—Sep. 1963.

Ultrasonics for Evaluation of Live Animal and Carcass Composition—J. R. Stouffer—Twelfth Research Conference—pp. 81-87.

Development and Application of Ultrasonic Methods for Measuring Fat Thickness and Rib-Eye Area in Cattle and Hogs—J. R. Stouffer et al—Journal of Animal Sci., vol. 20, No. 4, Nov. 1961.

Ultrasonic News—Winter 1960—vol. IV No. 4.

Comparison of Methods Used for Carcass Evaluation in Swine Doornenbal et al—Jou. of Ani. Sci., vol. 21, No. 3, Aug., 1962.

Techniques for the Estimation of the Composition of Meat Animals—J. R. Stouffer, pp. 207-219.

Status of the Application of Ultrasonics in Meat Animal Evaluation—J. R. Stouffer—pp. 161-173.

Ultrasonic Research in Europe—J. R. Stouffer—Mar.-Aug. 1962.

The Ultrasonic Approach to Measuring Fat and Muscling in Live Beef Cattle—J. R. Stouffer—pp. 34-35.

Carcass Evaluation and Its Research Applications—J. R. Stouffer—1961—pp. 32-36.

Application of Ultrasound in the Livestock and Meat Industry J. R. Stouffer—pp. 310-315.

Meat Evaluation in Live Animals—J. R. Stouffer—Frontiers in Food Research, Cornell University, Apr. 12-13, 1966, pp. 102-108.

Muscle Metabolism and Real-Time Ultrasound Measurement of Muscle and Subcutaneous Adipose Tissue Growth in Lambs Fed Diets Containing a Beta-Agonist—Stouffer et al—J. Anim. Sci. 1986. 63:1410-1417.

Estimating Fatness in Horses and Ponies—Stouffer et al Jour. Anim. Sci., vol. 43, No. 4 (1976).

Syllabus—2nd Annual AIUM Animal Ultrasound Seminar & Wet-Lab American Institute of ultrasound in Medicine—1990.

The Use of Ultrasound to Predict the Carcass Composition of Live Cattle—A Review—Animals Breeding Abstracts—G. Simm, vol. 51, No. 12, 1983.

Ultrasonic Determination of Body Composition—J. R. Stouffer Dec. 1968.

Studies on the Pathogenesis of Staphylococcal Osteomyelitis in Chickens,—I. Effect of Stress on Experimentally Induced Osteomyelitis Mutalib et al—Avian Dis., vol. 27, No. 1, Jan.-Mar. 1983 pp. 141-156.

Ultrasonics of Postmortem Detection of Animal Diseases and Abnormalities—J. R. Stouffer—Seminar for FSIS-USDA—Sep. 18, 1985.

Die Anwendung Non Ultraschallmessungen in den USA—J. R. Stouffer, pp. 64-70.

Real Time Ultrasound Evaluation—J. R. Stouffer—Jun. 1988.

Relationships of Empty-Body Composition and Fat Distribution to Live Animal and Carcass Measurements in Bos Indicus-Bos Taurus Crossred Cows—Holloway et al—pp. 1818-1826.

METHOD AND APPARATUS FOR POSITIONING AN ULTRASONIC TRANSDUCER FOR LONGITUDINAL SCANNING OF AN ANIMAL OR CARCASS

FIELD OF THE INVENTION

The present invention relates to ultrasonic animal and carcass evaluation, and more particularly relates to methods and apparatus for positioning an ultrasonic transducer for longitudinal scanning of an animal or carcass.

BACKGROUND OF THE INVENTION

Evaluating and grading meat animals, both live and slaughtered, have been historically performed by humans. Because of this it is very difficult to achieve accuracy, efficiency and consistency. Both producers and packers demand an objective means of classifying their animals accurately according to their carcass real values. However, since an accurate, quick, and consistent grading system has not been put into place, producers are not being paid for the true value of their animals. Currently, producers are paid on an average basis. The price differential between a high-yield and a low-yield grade is less than it should be. Therefore, it is important to the meat industries that improved or new technologies must be developed in their evaluation systems in order to be able to accurately measure the animal or carcass characteristics that are of significant value.

Typically, ultrasonic images of the Longissimus dorsi (rib eye muscle in beef and loin eye muscle in hogs) have been used to evaluate livestock. This has been done by positioning a linear transducer (scan line is in the same direction as the linear transducer) in either a perpendicular or parallel direction with respect to the backbone of the livestock. EPO Patent application publication number 0 337 661 A1, entitled "Method and apparatus for grading of live animals and animal carcasses" teaches method and apparatus for longitudinal (parallel to the backbone) scanning and image recognition to determine automatically fat and muscle characteristics. Wilson was not the first to use longitudinal scanning to evaluate carcasses, as shown by the Phd thesis by Wayne A. Gillis entitled "An Evaluation of Indices of Carcass Yield, Physical Composition and Chemical Composition in Swine; and Ultrasonic Measurement of the Longissimus Dorsi Area and Fat Thickness in Beef and Swine", which shows longitudinal scanning. Another group currently using longitudinal scanning is CSB-SYSTEM of America Corporation.

Neither Wilson, Gillis or CSB teach some of the problems associated with performing longitudinal scans or method or apparatus for consistently locating the transducer on the animal or carcass. One problem with longitudinal scanning occurs when the transducer is parallel to the back fat layers. Artifacts or multiples of the fat layers and the muscle/fat interface show up down in the image of the muscle layer. These multiples occur as a result of the sound waves rebounding directly back off of these layers and interfere with image recognition apparatus methods for determining muscle and fat composition. As can be seen by the advertising literature, the CSB system has the problem of artifacts as shown in the ultrasound image displayed on the first page.

Previously, many types of positioning apparatus have been implemented in for consistently positioning a transducer in a transverse (perpendicular) position along the backbone of an animal or carcass. For example, see U.S. Pat. Nos. 4,785,817; 4,099,420; 3,603,303; and 3,496,764 each granted to James R. Stouffer, one of the coinventors of the present invention. As shown in the sales catalog for ITHACO's SCANOGRAM, a guide-cam set Type C was available for linear scans consisting of a series of individual scans in a linear direction.

However, none of these positioning devices provided an apparatus for consistently positioning a transducer over the middle of the LD at about the last few ribs in a direction parallel to the backbone of the animal or carcass.

The present invention includes the discovery of the problems described herein and their solutions.

SUMMARY OF THE INVENTION

The method of positioning an ultrasonic transducer on an animal or carcass to be evaluated by ultrasonic detection equipment, is novel. The method comprises positioning the transducer over a last few ribs of the animal or carcass such that the transducer is parallel to a backbone of the animal or carcass and the transducer is not parallel to fat interfaces of the animal or carcass.

The transducer positioning apparatus is for positioning an ultrasonic transducer on an animal or carcass to be evaluated by ultrasonic detection equipment. The apparatus includes a support arm. A tail bone pin extends from the first end of the support arm and is for locating the transducer with respect to a tail region of the animal or carcass. A back position pin extends from the support arm and is for locating the transducer with respect to a backbone of the animal or carcass. A transducer support unit is included at the second end of the elongated support arm and is for positioning the transducer such that the transducer is parallel to the backbone.

It is a primary objective of this invention to provide apparatus and method for positioning an ultrasonic transducer in a longitudinal direction on an animal or carcass to be evaluated.

It is a further objective of this invention to provide apparatus and method for automatically positioning an ultrasonic transducer in a longitudinal direction on an animal or carcass to be evaluated.

These and other objects, features and advantages of the present invention should become apparent from the following description when taken in conjunction with the accompanying drawings.

DETAILED DESCRIPTION OF THE PREFERRED EMBODIMENT

Figure 1:
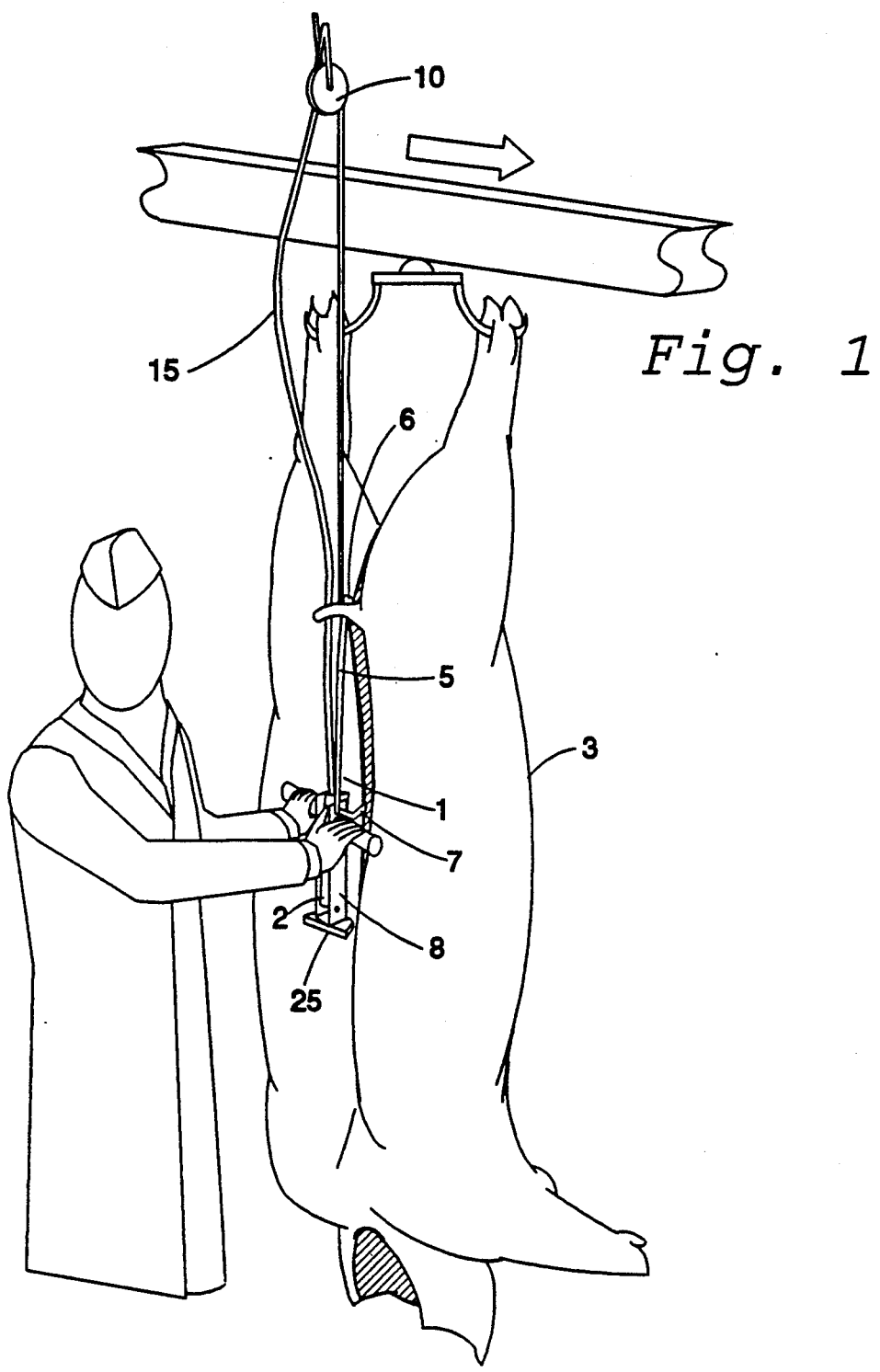
FIG. 1 is a perspective view of an inspection of a meat carcass with one embodiment of the positioning apparatus taught by the present invention.

For the purposes of promoting an understanding of the teachings of the present invention, references will now be made to the embodiments illustrated in the drawings and specific language will be used to describe these embodiments. It will nevertheless be understood that no limitation of the scope of the invention is thereby intended, alterations and further applications of the teachings of the present invention as illustrated and described hereinabove is anticipated by those skilled in this art.

FIG. 1 is a perspective view of an inspection of a meat carcass with one embodiment of the positioning apparatus 1 taught by the present invention. The transducer positioning apparatus 1 is for positioning an ultrasonic transducer 2 on an animal or carcass 3 to be evaluated by ultrasonic detection equipment. The apparatus includes a support arm 5. A tail bone pin 6 extends from the first end of the support arm 5 and is for locating the transducer 2 with respect to a tail region of the animal or carcass. A back position pin 7 extends from the support arm 5 and is for locating the transducer 2 with respect to a backbone of the animal or carcass. A transducer support unit 8 is included at the second end of the elongated support arm 5 and is for positioning the transducer 2 such that the transducer 2 is parallel to the backbone.

The positioning apparatus 1 is shown in use wherein the direction of the carcasses 3 are from the left to the right. The positioning apparatus 1 is therefore shown in an embodiment that is positioned on the right side of the carcass 3 so that the sideways motion of the carcass 3 will tend to catch both the tail pin 6 and the back pin 7. It is fully intended that one can make a mirror image of the device for carcasses travelling in opposite direction or make a device that can be switched back and forth for optimal use.

The positioning apparatus 1 includes means for attaching a spring loaded counter balance 10 to the positioning apparatus 1. This will reduce fatigue for the user. The transducer 2 is connected to ultrasound equipment by a cable 15. This cable 15 can be brought to the ultrasound equipment by the most efficient and safest means such that it does not interfere with the carcass 3 or the user.

Figure 2A:
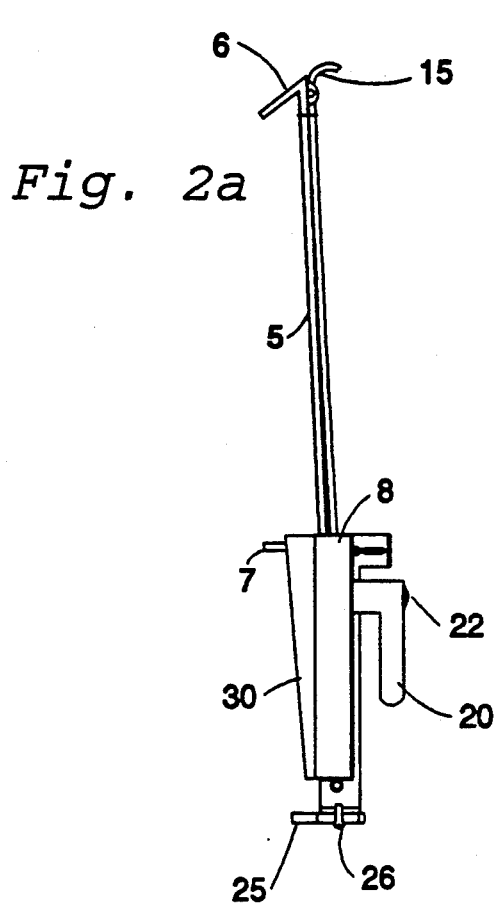
FIGS. 2a, 2b and 2c are a left side, right side and top views respectively of another embodiment of the positioning apparatus taught by the present invention with a pistol grip type handle.
Figure 2B:
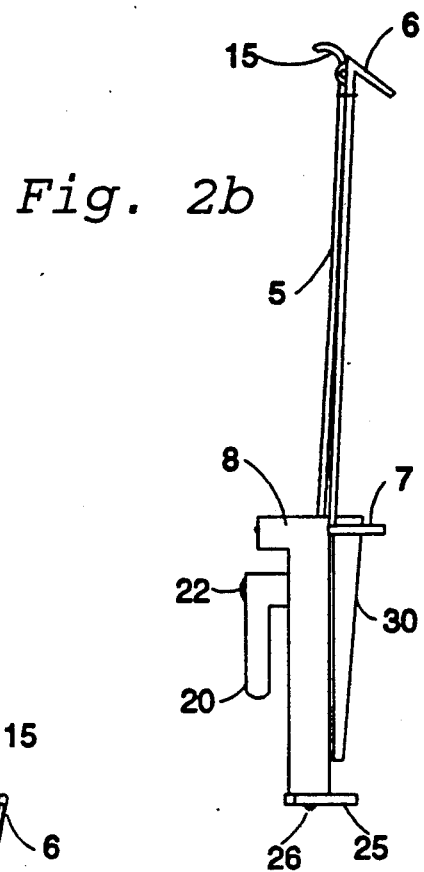
Figure 2C:
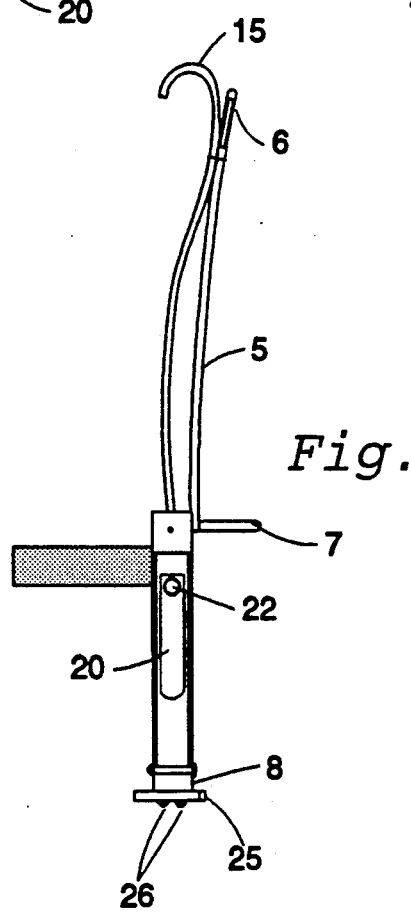

FIGS. 2a, 2b and 2c are a left side, right side and top views respectively of another embodiment of the positioning apparatus taught by the present invention with a pistol grip type handle 20. The means for attaching a counter balance to the positioning apparatus 1 are shown as a loop 21 and the first end of the elongated arm 5. The handle 20 includes an ultrasonic equipment switching device 22. The switching device 22 can be actuated to indicate to the ultrasonic equipment to evaluate the ultrasonic image when the transducer 2 is positioned properly, or in other words, freezing the current image for processing.

Figure 3:
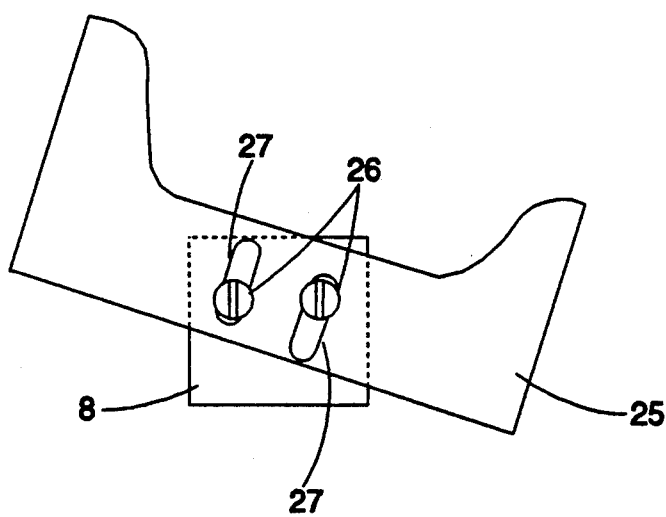
FIG. 3 shows the adjustable back edge of one embodiment of the positioning apparatus taught by the present invention.
Figure 4:
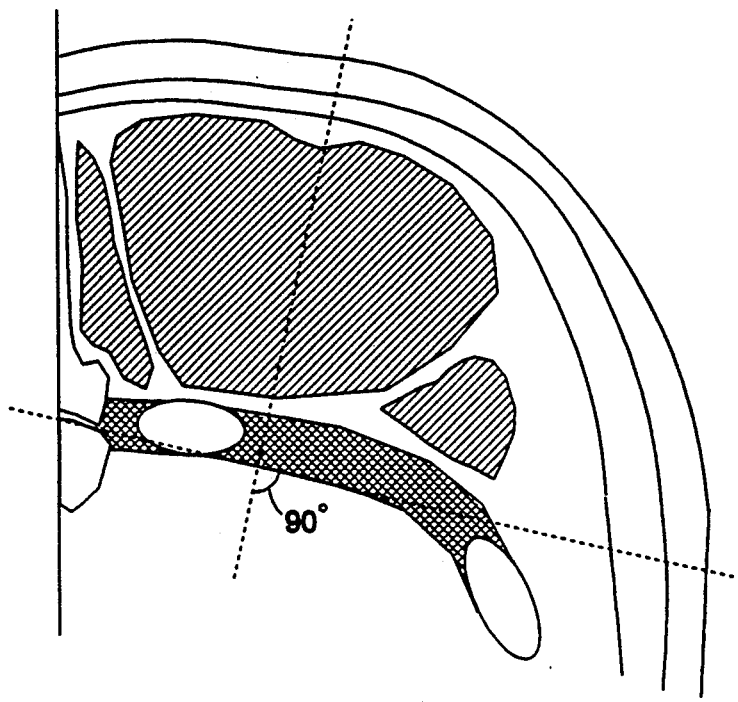
FIG. 4 shows a transverse cross section of a carcass showing the proper angle for ultrasonic scanning.

FIG. 3 shows the adjustable back edge 25 of the positioning apparatus 1 taught by the present invention. The back edge 25 is adjusted by position of screws 26 within slots 27 in the back edge 25. The screws 26 are tightened to secure the back edge in the desired position. This ability to adjust the angle of the transducer 2 can be very important. FIG. 4 shows a transverse cross section of a carcass showing the proper angle for ultrasonic scanning. The adjustable back edge can be used to position the transducer so that an image of the middle of the longissimus dorsi is seen in a line parallel to the backbone.

The transducer support unit 8 includes means for pivoting the transducer 2 such that a portion of the transducer 2 is initially brought into contact with the animal or carcass 3 and then the transducer 2 is brought into full contact with the or carcass 3 by pivoting the transducer 2. This way the user makes three contact point on the carcass 3: the tail pin 6, the back pin 7, and the back of the transducer 2 prior to making full contact with the transducer 2. The handle 20 can be used to pivot the transducer 2. This allows the user to be extremely efficient in proper placement of the transducer such that obtaining clear images and processing can be done at normal chain speeds. The positioning apparatus could include an automated transducer positioning device for bringing the transducer 2 into appropriate contact with the animal or carcass 3. Such a device would only need to make the three contact points discussed above and then bring the transducer 2 into full contact.

Figure 5:
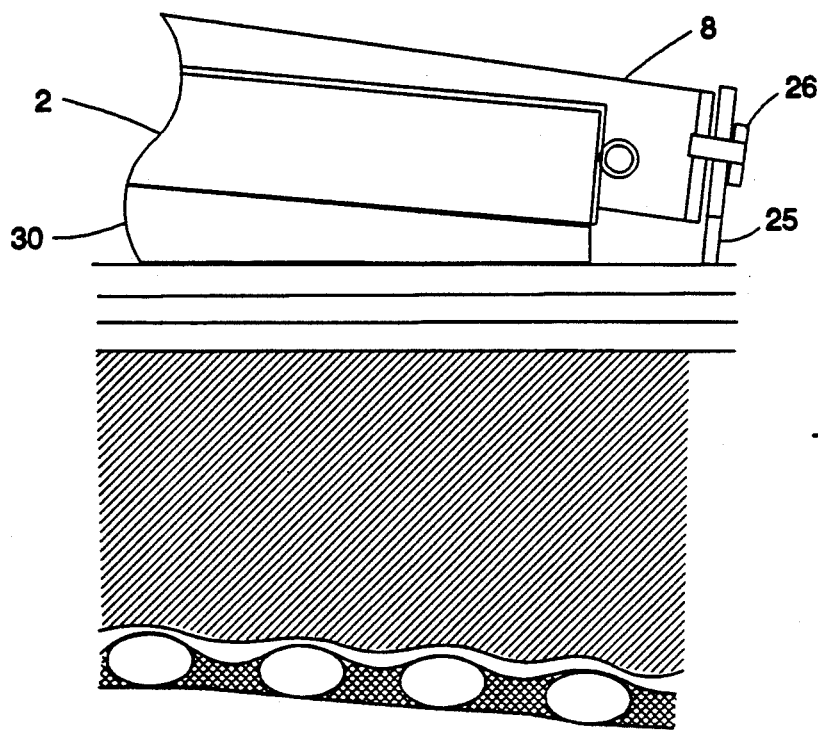
FIG. 5 shows a longitudinal cross section of a carcass with an ultrasonic probe.

FIG. 5 shows a longitudinal cross section of a carcass with an ultrasonic probe. The stand-off gel 30 is shown in clear detail. The positioning apparatus 1 positions the transducer 2 such that the transducer 2 is not parallel to fat interfaces of the animal or carcass thereby avoided the problem of artifacts. A good reference for this angle is to make the bottom of the transducer 2 parallel to the bottom of the rib line. The artifacts created by this line are too far down in the image to be a problem to automated image analyzers. The support unit 8 is designed to position the transducer 2 such that the transducer is actually constantly in contact with the angled stand-off gel 30 and it is the bottom of the stand-off gel that is brought into contact with the animal or carcass 3. Stand-off gels are commonly used to provide proper contact between transducer and subject. Superflab TM and Flexgel TM are both types of gels used for this purpose. The gel 30 is shaped for good contact with the carcass 3.

The method of positioning an ultrasonic transducer or an animal or carcass to be evaluated by ultrasonic detection equipment, is novel. The method comprises positioning the transducer 2 over a last few ribs of the animal or carcass such that the transducer 2 is parallel to a backbone of the animal or carcass and the transducer 2 is not parallel to fat interfaces of the animal or carcass.

The foregoing description has been directed to particular embodiments of the invention in accordance with the requirements of the Patent Statues for the purposes of illustration and explanation. It will be apparent, however, to those skilled in this art that many modifications and changes will be possible without departure from the scope and spirit of the invention. It is intended that the following claims be interpreted to embrace all such modifications.

I claim:

1. A transducer positioning apparatus for positioning an ultrasonic transducer on an animal or carcass to be evaluated by ultrasonic detection equipment, comprising:
    a) a support arm with a first and second end;
    b) a tail bone pin extending from said first end of said support arm for locating said transducer with respect to a tail region of the animal or carcass;

c) a back position pin extending from said support arm for locating said transducer with respect to a backbone of said animal or carcass; and d) a transducer support unit at said second end of said elongated support arm for positioning said transducer such that said transducer is parallel to said backbone.

2. The apparatus of claim 1 wherein said transducer support unit positions said transducer such that said transducer is not parallel to fat interfaces of said animal of carcass and is approximately parallel to a rib line of said animal or carcass.

3. The apparatus of claim 1 wherein said transducer support unit includes means for pivoting said transducer such that a portion of said transducer is initially brought into contact with said animal or carcass and then said transducer is brought into full contact with said animal or carcass by pivoting said transducer.

4. The apparatus of claim 3 further comprising handles for ease in positioning.

5. The apparatus of claim 4 wherein at least one said handles is located on said support unit such that said handle can be used to pivot said transducer.

6. The apparatus of claim 5 further comprising an ultrasonic equipment switching device on said handle such that said switching device can be actuated to indicate to said ultrasonic equipment to evaluate said ultrasonic image when said transducer is positioned properly.

7. The apparatus of claim 1 further comprising a counter balance to said apparatus.

8. The apparatus of claim 1 further comprising an automated transducer positioning device for bringing said transducer into appropriate contact with said animal or carcass.

9. The apparatus of claim 1 wherein said transducer support unit includes an adjustable back such that an appropriate angle of said transducer can be adjusted to consistently provide an image through a longissimus dorsi of said animal or carcass.

10. A method of positioning an ultrasonic transducer on an animal or carcass to be evaluated by ultrasonic detection equipment, comprising:

positioning said transducer over a last few ribs of said animal or carcass such that said transducer is parallel to the backbone of the animal or carcass and said transducer is not parallel to fat interfaces of said animal of carcass and is approximately parallel to a rib line of said animal or carcass.

* * * * *